US007317109B2

(12) United States Patent
Campbell et al.

(10) Patent No.: US 7,317,109 B2
(45) Date of Patent: *Jan. 8, 2008

(54) PYRROLIDINE COMPOUNDS AND METHODS FOR SELECTIVE INHIBITION OF DIPEPTIDYL PEPTIDASE-IV

(75) Inventors: David Alan Campbell, San Diego, CA (US); David T. Winn, San Diego, CA (US); Juan Manuel Betancort, San Diego, CA (US)

(73) Assignee: Phenomix Corporation, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/381,085

(22) Filed: May 1, 2006

(65) Prior Publication Data

US 2006/0264400 A1    Nov. 23, 2006

Related U.S. Application Data

(63) Continuation-in-part of application No. 10/514,575, filed on Oct. 27, 2005.

(60) Provisional application No. 60/519,566, filed on Nov. 12, 2003, provisional application No. 60/557,011, filed on Mar. 25, 2004, provisional application No. 60/592,972, filed on Jul. 30, 2004, provisional application No. 60/676,808, filed on May 2, 2005.

(51) Int. Cl.
*A61K 31/69* (2006.01)
*C07F 5/02* (2006.01)

(52) U.S. Cl. .......................... 548/405; 514/64

(58) Field of Classification Search ................. 548/405
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,572,912 A | 2/1986 | Yoshioka et al. |
| 4,681,893 A | 7/1987 | Roth |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,447,954 A | 9/1995 | Gribble et al. |
| 5,462,928 A | 10/1995 | Bachovchin et al. |
| 5,488,064 A | 1/1996 | Sher |
| 5,491,134 A | 2/1996 | Sher et al. |
| 5,541,204 A | 7/1996 | Sher et al. |
| 5,574,017 A | 11/1996 | Gutheil |
| 5,594,016 A | 1/1997 | Ueno et al. |
| 5,595,872 A | 1/1997 | Wetterau, II et al. |
| 5,614,492 A | 3/1997 | Habener |
| 5,631,224 A | 5/1997 | Efendic et al. |
| 5,686,104 A | 11/1997 | Mills et al. |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,952,301 A | 9/1999 | Drucker |
| 5,952,322 A | 9/1999 | Hoover et al. |
| 5,962,440 A | 10/1999 | Sulsky |
| 5,965,532 A | 10/1999 | Bachovchin |

(Continued)

FOREIGN PATENT DOCUMENTS

DE    19616486 A1    10/1997

(Continued)

OTHER PUBLICATIONS

"Avasimibe: Treatment of Lipoprotein Disorders, ACAT Inhibitor", *Drugs of the Future* 24(1), (1999), 9-15.

(Continued)

*Primary Examiner*—Laura L. Stockton
(74) *Attorney, Agent, or Firm*—Schwegman, Lundberg & Woessner P.A.

(57) ABSTRACT

The present invention is directed to pyrrolidinylaminoacetyl pyrrolidine boronic acid compounds that display selective, potent dipeptidyl peptidase IV inhibitory activity. These compounds are useful for the treatment of disorders that can be regulated or normalized via inhibition of DPP-IV including those characterized by impaired glycemic control such as Diabetes Mellitus and related conditions. The compounds can be administered alone or with another medicament that displays pharmacological activity for treatment of these and other diseases.

27 Claims, No Drawings

U.S. PATENT DOCUMENTS

| | | | |
|---|---|---|---|
| 5,998,463 | A | 12/1999 | Hulin et al. |
| 6,011,155 | A | 1/2000 | Villhauer |
| 6,040,145 | A | 3/2000 | Huber et al. |
| 6,107,317 | A | 8/2000 | Villhauer |
| 6,110,949 | A | 8/2000 | Villhauer |
| 6,124,305 | A | 9/2000 | Villhauer |
| 6,166,063 | A | 12/2000 | Villhauer |
| 6,172,081 | B1 | 1/2001 | Damon |
| 6,258,597 | B1 | 7/2001 | Bachovchin et al. |
| 6,300,314 | B1 | 10/2001 | Wallner et al. |
| 6,303,661 | B1 | 10/2001 | Demuth et al. |
| 6,355,614 | B1 | 3/2002 | Wallner |
| 6,380,398 | B2 | 4/2002 | Kanstrup et al. |
| 6,395,767 | B2 | 5/2002 | Robl et al. |
| 6,432,969 | B1 | 8/2002 | Villhauer |
| 6,617,340 | B1 | 9/2003 | Villhauer |
| 6,989,402 | B1 | 1/2006 | Hangeland et al. |
| 2003/0100563 | A1 | 5/2003 | Edmondson et al. |
| 2003/0153509 | A1 | 8/2003 | Bachovchin et al. |
| 2006/0258621 | A1 | 11/2006 | Campbell et al. |
| 2006/0264401 | A1 | 11/2006 | Campbell et al. |
| 2006/0276410 | A1 | 12/2006 | Campbell et al. |
| 2007/0185061 | A1 | 8/2007 | Campbell |

FOREIGN PATENT DOCUMENTS

| | | |
|---|---|---|
| EP | 0818448 B1 | 1/1998 |
| EP | 0896538 B1 | 2/1999 |
| EP | 0978279 A1 | 2/2000 |
| EP | 1041068 B1 | 4/2004 |
| WO | WO-89/03223 A1 | 4/1989 |
| WO | WO-91/16339 A1 | 10/1991 |
| WO | WO-93/08259 A2 | 4/1993 |
| WO | WO-93/10127 A1 | 5/1993 |
| WO | WO-95/11689 A1 | 5/1995 |
| WO | WO-95/15309 A1 | 6/1995 |
| WO | WO-96/39384 A1 | 12/1996 |
| WO | WO-96/39385 A1 | 12/1996 |
| WO | WO-97/12613 A1 | 4/1997 |
| WO | WO-97/12615 A1 | 4/1997 |
| WO | WO-97/21993 A2 | 6/1997 |
| WO | WO-98/00439 A2 | 1/1998 |
| WO | WO-98/19998 A2 | 5/1998 |
| WO | WO-98/50046 A1 | 11/1998 |
| WO | WO-99/00353 A1 | 1/1999 |
| WO | WO-99/03850 A1 | 1/1999 |
| WO | WO-99/26659 A1 | 6/1999 |
| WO | WO-99/38501 A2 | 8/1999 |
| WO | WO-99/43663 A1 | 9/1999 |
| WO | WO-00/34241 A1 | 6/2000 |
| WO | WO-00/38722 A1 | 7/2000 |
| WO | WO-00/47206 A1 | 8/2000 |
| WO | WO-03/045228 A2 | 6/2003 |
| WO | WO-03/045977 A2 | 6/2003 |
| WO | WO-2004/004661 A2 | 1/2004 |
| WO | WO-2005/047297 A1 | 5/2005 |

OTHER PUBLICATIONS

"International Search Report and Written Opinion for PTC Application No. PCT/US04/37820", (Mar. 10, 2005), 9 pgs.

Bachovchin, W. W., et al., "Inhibition of IgA1 Proteinases from *Neisseria gonorrhoeae* and *Hemophilus influenzae* by Peptide Prolyl Boronic Acids", *Journal of Biological Chemistry*, 265(7), (Mar. 5, 1990), 3738-3743.

Balkan, B., et al., "Improved Insulin Secretion and Oral Glucose Tolerance after In Vivo Inhibition of DPP-IV in Obese Zucker Rats", *Diabetologia, Suppl. 40, A131 Abstract*, (1977),1 page, 511.

Biller, S. A., et al., "Communications to the Editor: Isoprenold (Phosphinylmethyl)phosphonates as Inhibitors of Squalene Synthetase", *Journal of Medicinal Chemistry*, 31(10), (Oct. 1988), 1869-1871.

Biller, S. A., "Squalene Synthase Inhibitors", *Current Pharmaceutical Design*, 2(1), (1996), 1-40.

Corey, E. J., "Application of Unreactive Analogs of Terpenoid Pyrophosphates to Studies of Multistep Biosynthesis. Demonstration That "Presqualene Pyrophosphate" Is An Essential Intermediate on the Path to Squalene", *Journal of the American Chemical Society*, 98(5), (1976), 1291-1293.

Coutts, S. J., "Structure-Activity Relationships of Boronic Acid Inhibitors of Dipeptidyl Peptidase IV. 1. Variation of the $P_2$ Position of $X_{aa}$-boroPro Dipeptides", *J. Med. Chem.* 39(10), (1996), 2087-2094.

Coutts, S. J., et al., "Two Efficient Methods for the Cleavage of Pinanediol boronate Esters Yielding the Free Boronic Acids", *Tetrahedron Letters*, 35(29), (1994),5109-5112.

Deacon, C. F., et al., "Both Subcutaneously and Intravenously Administered Glucagon-Like Peptide I are Rapidly Degraded From the $NH_2$-Terminus in Type II Diabetic Patients and in Healthy Subjects", *Diabetes*, 44(9), Retrieved from the Internet: <http://gateway.ut.ovid.com.floyd.lib.umn.edu/gw2/ovidweb.cgi>, (1995), 1126-1131, (11 pgs.).

Deacon, C. F., et al., "Dipeptidyl Peptidase IV Inhibition as an Approach to the Treatment and Prevention of Type 2 Diabetes: a Historical Perspective", *Biochemical and Biophysical Research Communications 294*, (2002), 1-4.

Demuth, H.-U. , et al., "Rebuttal to Deacon and Holst: "Metformin Effects on Dipeptidyl Peptidase IV Degradation of Glucagon-like Peptide-1" Versus "Dipeptidyl Peptidase Inhibition as an Approach to the Treatment and Prevention of Type 2 Diabetes: a Historical Perspective"", *Biochemical and Biophysical Research Communications 296*, (2002), 229-232, p. 229 only.

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", *Cardiovascular Drug Reviews*, 16(1), (1998), 16-30.

Hara, S. , "Ileal $Na^+$/blle Acid Cotransporter Inhibitors", *Drugs of the Future*, 24(4), (1999), 425-430.

Hinke, S. A., et al., "Metformin Effects on Dipeptidyl-Peptidase IV Degradation of Glucagon-like Peptide-1", *Biochemical and Biophysical Research Communications 291*, (2002), 1302-1308.

Holst, Jens J., et al., "Perspectives in Diabetes: Inhibition of the Activity of Dipeptidyl-Peptidase IV as a Treatment for Type 2 Diabetes", *Diabetes*, vol. 47, From the Department of Medical Physiology, University of Copenhagen, Copenhagen, Denmark, (Nov. 1998), 1663-1670.

Kelly, T. A., et al., "Immunosuppresive Boronic Acid Dipeptides Correlation Between Conformation and Activity", *Journal of the American Chemical Society*, 115(26), (1993), 12637-12638.

Krause, B. R., "ACAT Inhibitors: Physiologic Mechanisms for Hypolipidemic and Anti-Atherosclerotic Activities in Experimental Animals", *Inflammation: Mediators and Pathways*, Ruffolo, Jr., et al., Editors, published by CRC Press, Boca Raton, FL, (1995), 173-198.

Kubota, T., et al., "Dipeptidyl Peptidase IV (DP IV) Activity in Serum and on Lymphocytes of MRL/Mp-*Iprllpr* Mice Correlates With Disease Onset", *Clin Exp Immunol 96*, (1994), 292-296.

McClard, R W., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", *J. Am. Chem. Soc.*, vol. 109, (1987), 5544-5545.

Murakami, K., "A Novel Insulin Sensitizer Acts as a Coligand for Peroxisome Proliferation-activated Receptor-α (PPAR-α) and PPAR-γ —Effect on PPAR-α Activation on Abnormal Lipid Metabolism in Liver of Zucker Fatty Rats", *Diabetes*, vol. 47, (Dec. 1998), 1841-1847.

Nicolosi, R. J., et al., "The ACAT Inhibitor, CI-1011 is Effective in the Prevention and Regression of Aortic Fatty Streak Area in Hamsters", *Atherosclerosis 137*, (1998),77-85.

Ortiz De Montellano, P. R., "Inhibition of Squalene Synthetase by Farnesyl Pyrophosphate Analogues", *Journal of Medicinal Chemistry*, 20(2), (1977), 243-249.

Pauly, R. P., et al., "Inhibition of Dipeptidyl Peptidase IV (DP IV) in Rat Results in Improved Glucose Tolerance", *Abstracts from the 11th International Symposium on Regulatory Peptides*, (1996), p. 148.

Rosenblum, S. B., "Discovery of 1-(4-Fluorophenyl)-(3*R*)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem. 41*, (1998), 973-980.

Salisbury, B. G., "Hypocholesterolemic Activity of a Novel Inhibitor of Cholesterol Absorption, SCH 48461", *Atherosclerosis 115*, (1995), 45-63.

Sendobry, S. M., "Attenuation of Diet-Induced Atherosclerosis in Rabbits with a Highly Selective 15-lipoxygenase Inhibitor Lacking Significant Antioxidant Properties", *British Journal of Pharmacology 120*, (1997), 1199-1206.

Sliskovic, D. R., "ACAT Inhibitors: Potential Anti-atherosclerotic Agents", *Current Medicinal Chemistry*, 1(3), (1994), 204-225.

Smith, C., "RP 73163: A Bioavailable Alkylsulphinyl-Diphenylimidazole ACAT Inhibitor", *Bioorganic & Medicinal Chemistry Letters*, 6(1), (1996), 47-50.

Stout, D. M., et al., "Inhibitors of Acyl-CoA: Cholesterol O-Acyl Transferase (ACAT) as Hypocholesterolemic Agents. 6. The First Water-Soluble ACAT Inhibitor With Lipid-Regulating Activity", *Chemtracts-Organic Chemistry*, vol. 8, (1995), 359-362.

Tanaka, S., et al., "Suppression of Arthritis by the Inhibitors of Dipeptidyl Peptidase IV", *International Journal of Immunopharmacology*, 19(1), (1997), 15-24.

Tanaka, S., et al., "Suppression of Arthritis by the Inhibitors of Dipeptidyl Peptidase IV", *Ensho—Japanese Journal of Inflammation*, 18(3), (1998), 199-202.

Application Serial No. 04810839.3 (EPO), Non-Final Office Action mailed Jul. 18, 2007, 4 p.

Application Serial No. 04810839.3 (EPO), Supplemental European Search Report mailed Dec. 13, 2006, 3 p.

PYRROLIDINE COMPOUNDS AND METHODS FOR SELECTIVE INHIBITION OF DIPEPTIDYL PEPTIDASE-IV

CROSS REFERENCE TO RELATED APPLICATIONS

This application is a continuation-in-part of U.S. application Ser. No. 10/514,575, filed on Oct. 27, 2005, which is a national stage application of PCT/US04/037820, which claims priority to U.S. provisional application No. 60/519,566, filed on Nov. 12, 2003; U.S. provisional application No. 60/557,011, filed on Mar. 25, 2004; and U.S. provisional application No. 60/592,972, filed on Jul. 30, 2004. This application is also a continuation-in-part of U.S. application Ser. No. 60/676,808, filed on May 2, 2005. These applications are incorporated herein by reference.

FIELD OF THE INVENTION

The present invention relates to a pyrrolidinylaminoacetyl pyrrolidine boronic acid compound and its use as a selective inhibitor of post-proline/alanine cleaving amino-dipeptidases, particularly dipeptidyl peptidase-IV (DPP-IV). The invention also relates to methodology for employing a pyrrolidine compound, alone or with another medicament, to treat a DPP-IV-related disease, including but not limited to disorders characterized by impaired glycemic control, especially Diabetes Mellitus and related conditions. Thus, the invention has applications in the medicinal, chemical, pharmacological, and medical fields.

BACKGROUND OF THE INVENTION

Dipeptidyl peptidase-IV (DPP-IV) is a serine protease that belongs to a group of post-proline/alanine cleaving amino-dipeptidases. DPP-IV catalyzes the release of an N-terminal dipeptide of any configuration from proteins, and preferably, the dipeptide contains an N-terminal penultimate proline or alanine.

The physiological role of DPP-IV has not been established fully. It is believed to play an important role in regulatory peptide metabolism, which, among other things, controls various physiological functions including but not limited to glycemic control and insulin sensitivity. In particular, DPP-IV has been implicated in the control of glucose metabolism because its substrates include the insulinotropic hormones, glucagon like peptide-1 (GLP-1) and gastric inhibitory peptide (GIP), which are inactivated by removal of their two N-terminal amino acids.

In vivo administration of synthetic inhibitors of DPP-IV prevents N-terminal degradation of insulinotropic hormones including, GLP-1 and GIP, resulting in higher plasma concentrations of these hormones, increased insulin secretion and, consequent improved glucose tolerance. Therefore, such inhibitors have been proposed for the treatment of patients with impaired glycemic control such as Diabetes Mellitus and related conditions.

This proposal has significant difficulties, however. Additional dipeptide cleaving amino-dipeptidases have also been discovered, including DPP-VII, DPP-VIII, DPP-IX, and fibroblast activation protein (FAP), which can have substrate and inhibitor specificity similar to DPP-IV. The precise physiological role of each of these dipeptide cleaving enzymes is not well defined. But, their propensity to cleave N-terminus dipeptides from proteins in general indicates that these amino-dipeptidases are involved in many physiological cycles. Thus, the difficulty concerning inhibitors of DPP-IV is that they can also affect the other members of the enzyme group. The evidence indicates that, for example, other inhibitors of DPP-IV, which also inhibit the other amino-dipeptidases such as DPP-VIII, will cause toxic effects in animals.

Accordingly, a need exists for compounds that are useful for inhibiting DPP-IV without an adverse event profile that precludes chronic administration.

SUMMARY OF THE INVENTION

The present invention is directed to a selective DPP-IV inhibitor and methods of use that are effective in treating conditions that may be regulated or normalized by inhibition of DPP-IV. More particularly, the invention is directed to a pyrrolidinylaminoacetyl pyrrolidine boronic acid compound. This pyrrolidinylaminoacetyl pyrrolidine boronic acid compound is useful at effective doses for treatment of malconditions associated with DPP-IV activity and is a selective inhibitor of DPP-IV.

A pyrrolidinylaminoacetyl boronic acid compound of the invention (hereinafter the pyrrolidine compound of the invention) has a structure represented in part by Formula I.

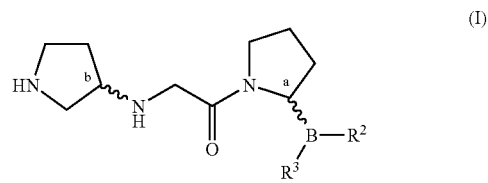

(I)

The substituents and bond designations of formula I include $R^2$ and $R^3$, which, independently or together, are —OH, —O⁻M⁺ wherein M⁺ is a cation, a hydroxyl bearing a boronic acid protecting group, or a group capable of being hydrolyzed to a hydroxyl group in an aqueous solution at physiological pH or in biological fluids; and the wavy lines at asymmetric carbons $C^a$ and $C^b$, which independently indicate for each asymmetric carbon an R configuration, an S configuration, or a mixture of both configurations such that all stereoisomers and all stereomeric mixtures are included. Also included within the scope of the invention are a cyclic isomer thereof, any pharmaceutically acceptable salt thereof, any prodrug thereof, and any solvate thereof.

A pyrrolidine compound of the invention may exist in either of two forms, the linear form represented by formula I above and the cyclic isomer form represented by formula V below.

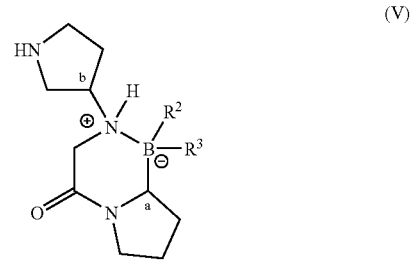

(V)

The cyclic isomer form and the linear form are in thermodynamic equilibrium when in solution. The equilibrium shifts depending upon pH. Thus, the predominance of one form over the other in solution depends upon the pH so that at acidic pH, the linear isomer predominates while at basic pH, the cyclic isomer predominates. The linear and cyclic isomers are also stable such that either form may be isolated as a solid. The isolated cyclic isomer can function as a prodrug.

The invention also is directed to a pharmaceutical composition containing a pyrrolidine compound of the invention and a pharmaceutical carrier. The pharmaceutical composition may be formulated to be dosed by any administrative route including but not limited to parenteral injection, oral, buccal, rectal and the like.

The invention is as well directed to a method of treatment of a malcondition that can be regulated or normalized via inhibition of DPP-IV. The method involves administration of an effective amount of a pyrrolidine compound of the invention, such as would be present in a pharmaceutical composition of the invention, to mammals, especially humans, to affect a malcondition that can be regulated or normalized via inhibition of DPP-IV. Preferably, an effective amount of a pyrrolidine compound of the invention exhibits lower toxicity than do non-selective inhibitors of DPP-IV, particularly in comparison to boronic acid inhibitors of DPP-IV that also display inhibition of other DPP enzymes and FAP. Therefore, the invention is directed to methods for selectively inhibiting DPP-IV including administering to a patient in need of such treatment a therapeutically effective amount of a pyrrolidine compound of the invention.

The invention further is directed to a pharmaceutical combination of a pyrrolidine compound of the invention and one or more other medicaments that are useful for treatment of a malcondition that can be regulated or normalized via inhibition of DPP-IV. Such malconditions are associated with impairments in glycemic control especially Diabetes Mellitus and related conditions. A pharmaceutical combination may be formulated according to the invention as a pharmaceutical composition.

The invention is also directed to a process for preparing a pyrrolidine compound of the invention, a method for preparing a pharmaceutical composition of the invention, and the use of a pyrrolidine compound of the invention in a method for the preparation of a medicament for treating a malcondition that can be regulated or normalized via inhibition of DPP-IV.

DEFINITIONS

The term "absolute configuration" in connection with an asymmetric carbon is determined by considering the tetrahedral shape of the asymmetric carbon bonds, assigning a priority of 1 through 4 to each of the groups bound to the asymmetric carbon with the group having the highest atomic number having the first priority. If the tetrahedron is viewed from a side remote from group 4, an R absolute configuration is assigned when groups 1-3 are in a clockwise arrangement and an S absolute configuration is assigned when groups 1-3 are in a counterclockwise arrangement.

The term "asymmetric carbon" means a carbon atom covalently bound to four different groups.

The term "beta cell degeneration" is intended to mean loss of beta cell function, beta cell dysfunction, and death of beta cells, such as necrosis or apoptosis of beta cells.

The term "Diabetes Mellitus and related conditions" refers to Type 1 diabetes, Type 2 diabetes, gestational diabetes, MODY, impaired glucose tolerance, impaired fasting glucose, hyperglycemia, impaired glucose metabolism, insulin resistance, obesity, diabetic complications, and the like.

The term "diabetic complications" refers to conditions, diseases and maladies associated with diabetes including retinopathies, neuropathies, nephropathies, cardiomyopathies, dermopathies, arthrosclerosis, coronary artery disease and other known complications of diabetes.

The term "diastereomer" means one member of a group of two or more stereoisomers having at least two asymmetric carbons such that these stereoisomers are not mirror images of each other.

The terms "DPP-VII, DPP-VIII, DPP-IX and FAP" mean respectively amino dipeptidyl peptidase VII, VIII, IX and fibroblast activation protein. The DPP enzymes cleave dipeptide moieties at the N-terminus of their protein or oligopeptide substrates. In particular, the term "DPP-IV" denotes dipeptidyl peptidase IV (EC 3.4.14.5; DPP-IV), also known as "CD-26." DPP-IV preferentially cleaves a dipeptide from the N terminus of a polypeptide chain containing a proline or alanine residue in the penultimate position.

The term "enantiomer" means one member of a pair of stereoisomers having the same molecular structure and at least one asymmetric carbon such that the stereoisomers of the pair are the mirror images of each other. If the enantiomer contains two or more asymmetric carbons, the enantiomeric pair will have opposing asymmetry at each asymmetric carbon.

The term "group that can be hydrolyzed to a hydroxyl" as used herein refers to an ester group formed from the combination of an aliphatic or aromatic alcohol or diol and a boronic acid.

The term "inhibitor" (and its corresponding verb and gerund) means a compound that will reversibly, irreversibly or temporarily interact with an enzyme so as to reduce, modify, slow down or block its enzymatic activity upon its normal substrate. The interaction may occur within or at the enzymatic site or at an allosteric site associated with the enzyme.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T.W. Greene, P. G. Wuts, "Protective Groups In Organic Synthesis, 3$^{rd}$ Ed." (John Wiley & Sons, New York (1999)), which is hereby incorporated by reference. N-protecting groups include acyl groups such as formyl, acetyl, propionyl, pivaloyl, t-butylacetyl, 2-chloroacetyl, chloracetyl, 2-bromoacetyl, trifluoroacetyl, trichloracetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, αα-dimethyl-3,5-dimethoxvbenzyloxvcarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

The term "optically active" means an organic compound containing at least one asymmetric carbon such that a solution of the organic compound will rotate plane polarized light.

The term "optically active mixture" means a mixture of optically active compounds in solution that will rotate plane polarized light. The optically active mixture may be a mixture of diastereomers or an unequal mixture of enantiomers.

The term "pharmaceutical salt" means a salt with an inorganic base, organic base (including basic amino acids), inorganic acid, and organic acid (including acidic amino acids). Included as examples of inorganic bases are alkali metals such as lithium, sodium or potassium; alkaline earth metals such as calcium and magnesium or aluminum; and ammonia. Included as examples of organic bases are trimethylamine, triethylamine, pyridine, picoline, ethanolamine, diethanolamine, and triethanolamine. Included as examples of inorganic acids are the instant invention includes, for example, hydro-halogen acids such as hydrochloric acid, hydroboric acid, nitric acid, sulfuric acid, and phosphoric acid. Included as examples of organic acids are mono, di and tri carboxylic or sulfonic acids of 1 to 20 carbons, optionally containing 1 to 6 hydroxyl groups. Included as examples of basic amino acids are arginine, lysine and ornithine. Included as examples of acidic amino acids are aspartic acid and glutamic acid. Further examples of pharmaceutically acceptable salts include the pharmaceutically acceptable salts listed in Journal of Pharmaceutical Science, 66, 2 (1977) which are known to the skilled artisan.

The term "prodrug" means a pharmaceutically acceptable compound that will convert to the active ingredient or an active metabolite thereof upon administration of the prodrug to a living organism, preferably a mammal, more preferably a human. The conversion may occur by enzymatic action, chemical hydrolysis, oxidation, reduction or any other in vivo physiological process for chemical or biochemical reaction.

The term "racemic mixture" means an enantiomeric pair of equal proportions such that they cancel each other's rotation of plane polarized light.

A singular term such as "a pyrrolidine compound of the invention" includes the plural such as the various species of the pyrrolidine compound of the invention as well as mixtures thereof. A plural term such as "pyrrolidine compounds of the invention" includes the individual species as well as the plural indicated by this term, and also mixtures thereof.

The term "selectivity ratio" refers to the $IC_{50}$ value generated in a biochemical assay measuring inhibition of DPP-IV compared to the $IC_{50}$ value generated in a biochemical assay measuring inhibition of another DPP family member (e.g. DPP-VII, DPP-VIII, DPP-IX or FAP) whereby the ratio is obtained by dividing the $IC_{50}$ value of DPP-VII, DPP-VIII, DPP-IX or FAP by the $IC_{50}$ value for DPP-IV.

The term "solvate" means a solid, crystalline form of a compound which also incorporates molecules of a solvent into the crystal structure. Organic solvents as well as water are included. Another description of a water solvate is a hydrate or hydrated form.

The term "stereoisomer" means one of the absolute configurations of a single organic molecule having at least one asymmetric carbon. Included within the definition of a stereoisomer are enantiomers and diastereomers. One stereoisomer has one absolute configuration about each of the asymmetric carbons of the organic molecule. An organic molecule with one asymmetric carbon presents two stereoisomers. An organic molecule with two asymmetric carbons presents four stereoisomers. An organic molecule with three asymmetric carbons presents eight stereoisomers. Projecting plane polarized light through a solution containing one stereoisomer will cause rotation of the polarized plane.

The term "stereomeric mixture" means a mixture of two or more stereoisomers and includes enantiomers, diastereomers and combinations thereof. The stereomeric mixture may or may not be optically active.

The term "stereomeric purity" at a given percentage means that the designated stereoisomer predominates at that given percentage in a mixture of stereoisomers.

Unless otherwise specifically stated, the definitions of terms for chemical groups, functional groups, moieties and chemical reactions described herein follow the definitions provided in such organic chemistry textbooks and treatises as "Basic Principles of Organic Chemistry", Roberts and Caserio, W.A. Benjamin & Co. New York, N.Y., 1965; "Advanced Organic Chemistry", $4^{th}$ edition, Jerry March, Wiley Interscience, New York, N.Y. 1992; T. W. Greene, P. G. Wuts, "Protective Groups In Organic Synthesis, $3^{rd}$ Ed." (John Wiley & Sons, New York (1999), and Hawley's Condensed Chemical Dictionary, $11^{th}$ Ed., Sax and Lewis, Van Nostrand, Reinhold, New York, N.Y., 1987. Moreover, the definitions for stereochemical terms are based upon "Stereochemistry of Carbon Compounds", Ernest Eliel, McGraw-Hill publisher, New York, N.Y. 1962. The disclosures of these text books are incorporated herein by reference.

DETAILED DESCRIPTION OF THE INVENTION

A pyrrolidinylaminoacetyl pyrrolidine boronic acid compound of the invention (pyrrolidine compound of the invention) has the linear or cyclic isomer structure depicted by formulas I and V above. All stereoisomers, stereomeric mixtures, pharmaceutically acceptable salts, solvates and prodrugs are included as embodiments of the "pyrrolidine compounds of the invention" (which is also termed "pyrrolidine compound" or "pyrrolidine compounds" herein). A pharmaceutical composition including a pyrrolidine compound of the invention and a pharmaceutically acceptable pharmaceutical carrier is an additional aspect of the invention. Also included is a pharmaceutical combination of a pyrrolidine compound of the invention and a second medicament known to be useful in the treatment of malconditions characterized by impaired glycemic control, especially Diabetes Mellitus and related conditions. A pharmaceutical combination may be formulated as a pharmaceutical composition of the pyrrolidine compound, the second medicament and a pharmaceutically acceptable carrier.

The embodiments of the pyrrolidine compound of the invention include the borate esters and boronic acid groups such that $R^2$ and $R^3$ of formulas I and V, independently or together, are —OH, —O⁻M⁺ wherein M⁺ is a cation, a hydroxyl bearing a boronic acid protecting group, or a group capable of being hydrolyzed to a hydroxyl group in an aqueous solution at physiological pH or in biological fluids. When $R^2$ and $R^3$ are groups that can be hydrolyzed to hydroxyls, they may be formed from mono-alcohols and diols of 1 to 15 carbons and the alcohols and diols may be linear, branched, cyclic or aromatic, and may optionally be substituted with ester and/or amide groups. Examples include (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol.

Surprisingly, it has been discovered that a pyrrolidine compound of the invention displays selectivity for DPP-IV relative to other dipeptidyl peptidase enzymes. By selectivity for DPP-IV it is meant that the pyrrolidine compound of the invention more strongly inhibits DPP-IV, than at least one closely related enzyme such as DPP-VII, DPP-VIII, DPP-IX and FAP. While not wishing to be bound by any theory, it is believed that this unexpected selectivity for DPP-IV results in an improved therapeutic profile with diminished side-effects for the pyrrolidine compound of the invention compared with other boronic acid inhibitors and compared to any other non-selective DPP-IV inhibitor. In particular it is believed that potent inhibition of DPP-VIII by other inhibitors correlates with the acute toxicity observed in animal studies. As detailed in the following Examples section, administering a compound with DPP-IV and DPP-VIII inhibitory activity to dogs leads to severe emesis and diarrhea. The same compounds administered to some strains of rats resulted in death. The pyrrolidine compound of the invention avoids significant inhibition of DPP-VIII and therefore avoids the toxicities observed in both dog and rat.

Synthesis of the Pyrrolidine Compounds of the Invention

The invention also relates to processes for preparing a pyrrolidine compounds of the invention. As shown below and as described in the examples, the pyrrolidine compound of the invention is prepared by reacting a pyrrolidine, suitably protected with a standard protecting group such as Boc-, Fmoc-, Cbz- or the like, with sec-BuLi/TMEDA followed by a boron source such as B(OCH$_3$)$_3$, to provide the boronic ester derivative. Acid hydrolysis of the methyl esters with HCl provides the boronic acid intermediate 1. Reaction of 1 with (+) pinanediol, deprotection of the amino protecting group, and recrystallization provides the pinanediol ester 2 as an isomerically pure salt.

Intermediate 2 is useful for the synthesis of a pyrrolidine compound of the invention. For example, N-acylation of 2 with chloroacetyl chloride provides the α-chloro amide 3. Treatment of 3 with Na$_2$CO$_3$ and a pyrrolidinylamine, hydrolysis of the pinanediol boronic ester, and N-deprotection provides a pyrrolidine compound of the invention, 4.

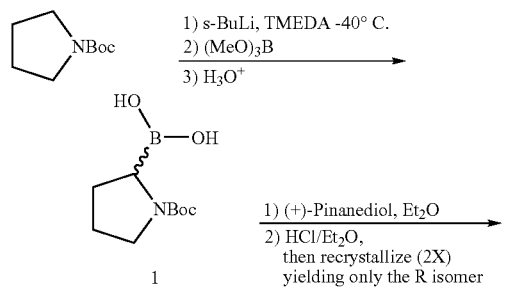

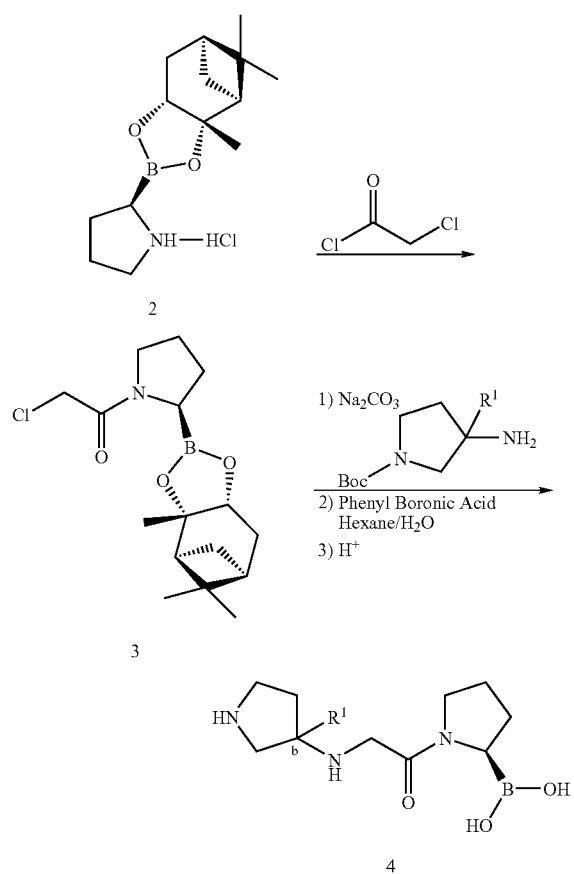

wherein R$^1$ is hydrogen. The S stereoisomer of 2 or a mixture of stereoisomers can be obtained by appropriate manipulation of the recrystallization step, which includes a resolution using an optically active pinanediol. Use of an R or S stereoisomer of the amino pyrrolidine reagent for reaction with 3, or use of a stereomeric mixture thereof will yield the desired stereochemistry at the C$^b$ asymmetric carbon as shown in structure 4.

Thus, another aspect of the invention provides a process for preparing a pyrrolidine compound of the invention including coupling a reactive compound of Formula II:

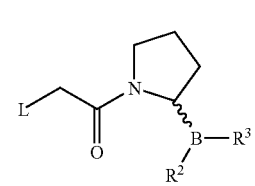

wherein L is a leaving group such as a halogen, mesylate, tosylate, triflate or the like; and R$^2$ and R$^3$ are independently or together are —OH, —O$^-$M$^+$ wherein M$^+$ is a cation, a hydroxyl bearing a boronic acid protecting group, or a group capable of being hydrolyzed to a hydroxyl group in an aqueous solution at physiological pH or in biological fluids;

with a compound of Formula III

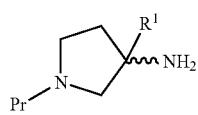

wherein Pr is an N-protecting group such as Boc, Cbz, Fmoc, benzyl or the like; and $R^1$ is hydrogen; to provide an ester derivative of the pyrrolidine compound of the invention. The resulting boronic ester derivative of the pyrrolidine compound of the invention may be deprotected to remove Pr and to recover the pyrrolidine compound of the invention as an ester, a free acid or as a salt. In some embodiments, L is halogen, including but not limited to Cl. In others $R^2$ and $R^3$ are each methoxy or together are pinanedioxy, e.g. (+)-pinanedioxy as in compound 3 above. In still others, Pr is Boc.

An alternative synthesis of a pyrrolidine compound of the invention is provided in U. S. patent application Ser. No. 60/704,3 80, filed Aug. 1, 2005 and entitled "Methods of Preparing Heterocyclic Boronic Acids and Derivatives Thereof."

A pyrrolidine compound of the invention may be formed as a pharmaceutically acceptable salt. The pharmaceutical salt may be obtained as the direct product of compound synthesis. In the alternative, the free base may be dissolved in a suitable solvent containing the appropriate acid (or vice versa), and the salt isolated by evaporating the solvent or otherwise separating the salt and solvent. The processes for forming a pharmaceutically acceptable salt from an amine compound such as a pyrrolidine compound of the invention are well-known in the art. See, for example, "The Practice of Medicinal Chemistry, Second Edition", by Camille G. Wermuth, Academic Press, New York, N.Y., 1996.

A pyrrolidine compound of the invention may form solvates with standard low molecular weight solvents, including water to yield hydrates, using methods known to the skilled artisan. These processes for forming solvates are also well-known in the art. See, for example "The Practice of Medicinal Chemistry" cited above.

It is to be understood that the invention extends to all of the stereoisomers of a pyrrolidine compound, including enantiomers, diastereomers, as well as the racemates and stereoisomeric mixtures. The mixtures may or may not be optically active.

In some embodiments, a pyrrolidine compound of the invention may have an optical purity of at least about 55%, preferably 80%, more preferably 90 wt %, most preferably 98% or more of a single stereoisomer. In other embodiments, the pyrrolidine compound is an optically-enriched enantiomer. In still other embodiments, the pyrrolidine compound is a mixture of stereoisomers including but not limited to unequal mixtures of enantiomers and/or mixtures of diastereomers.

Method/Use of a Pyrrolidine Compound of the Invention

The method of treatment and use of a pyrrolidine compound of the invention is based upon inhibition of dipeptidyl peptidase-IV by contact of the enzyme, dipeptidyl peptidase-IV, with a pyrrolidine compound in any of its forms as described above. The contact may be accomplished in vitro such as through a diagnostic test or a screening test, or in vivo through an appropriate administrative route as discussed below.

The in vivo methods according to the invention involve a pyrrolidine compound of the invention in its role as a selective inhibitor of DPP-IV. For example, the invention provides a method of treatment of a mammal (such as a human) suffering from a malcondition that can be regulated or normalized via inhibition of DPP-IV such as any malcondition characterized by impaired glycemic control, especially Diabetes Mellitus and related conditions by administering an effective amount of a pyrrolidine compound of the invention to treat, control, ameliorate or prevent the malcondition. These malconditions are known to be the result, at least in part, of the presence, or altered activity, of peptides regulated by the enzyme DPP-IV, especially in the context of its physiological role in glycemic control. These methods of the invention are accomplished by administering to the mammal (e.g., a human) an effective amount of a pyrrolidine compound of the invention. Treatment is affected by inhibition of DPP-IV. Administration is typically accomplished through use of a pharmaceutical composition containing a pyrrolidine compound of the invention.

The method of the invention further includes a method for selectively inhibiting DPP-IV over related enzymes. In some embodiments of the methods for treatment, DPP-IV is inhibited by greater than 5-fold relative to one or more other dipeptidyl peptidases. In other embodiments, DPP-IV is inhibited by greater than 10-, 20-, or even 50-fold or more over other dipeptidyl peptidases. Exemplary other dipeptidyl peptidases include DPP-VII, DPP-VIII, DPP-IX, and FAP. For example, a pyrrolidine compound of the invention can selectively inhibit DPP-IV over dipeptidyl peptidase-VII, or DPP-IV over dipeptidyl peptidase-VIII, or DPP-IV over dipeptidyl peptidase-IX, or DPP-IV over fibroblast activation protein (FAP). In additional embodiments, a pyrrolidine compound of the invention selectively inhibits DPP-IV over dipeptidyl peptidase-VIII and fibroblast activation protein. In other embodiments, the pyrrolidine compound of the invention selectively inhibits DPP-IV over dipeptidyl peptidase-VII, dipeptidyl peptidase-VIII, and fibroblast activation protein. This selectivity applies to in vitro and to in vivo situations. In particular, it has been determined in an in vivo protocol study in humans that a pyrrolidine compound of the invention maintained selectivity for inhibition of DPP-IV over the other amino dipeptidyl peptidases. Preferably, the DPP-IV selectivity is shown relative to DPP-VIII.

For in vivo use as a DPP-IV inhibitor, a pyrrolidine compound of the invention may be formulated in any manner as described herein and administered in an effective amount to a patient (human) suffering from a malcondition that can be regulated or normalized by inhibition of DPP-IV, especially a malcondition characterized by impaired glycemic control, especially Diabetes Mellitus and related conditions. For example, the malcondition can be Type 1 diabetes, Type 2 diabetes, gestational diabetes, MODY, impaired glucose tolerance, impaired fasting glucose, hyperglycemia, impaired glucose metabolism, impaired glucose tolerance (IGT) and its progression to Type II diabetes, hyperinsulinemia, obesity, beta cell degeneration (in particular apoptosis of beta cells), the progression of non-insulin-requiring Type II diabetes to insulin requiring Type II diabetes; loss of the number and/or the size of beta cells in a mammalian subject, and diabetic complications such as retinopathy, neuropathy, nephropathy, cardiomyopathy, dermopathy, diabetes related infection, atherosclerosis, coronary artery disease, stroke and similar malconditions.

In other embodiments of method of treatment according to the invention, insulin resistance is a component of the malcondition that can be regulated or normalized by inhibition of DPP-IV. For example, the malconditions can be impaired fasting glucose, impaired glucose tolerance, polycystic ovarian syndrome and the like. In yet other embodiments, the malcondition that can be regulated or normalized by inhibition of DPP-IV involves a decrease of islet neogenesis, β-cell survival, or insulin biosynthesis.

The administered dose of a pyrrolidine compound of the invention will be carefully adjusted according to age, weight and condition of the patient, as well as the route of administration, dosage form and regimen and the desired result. The ultimate choice of dosage, route and pharmaceutical formulation will determined by the patient's attending physician, whose wisdom and judgment will guide this process. The dose for adults may range from about 0.5 to about 2,000 mg per day, preferably about 10 mg to about 1000 mg per day, more preferably about 50 mg to about 750 mg per day which can be administered in a single dose or in the form of multiple doses given up to 4 times per day.

The use of a pyrrolidine compound of the invention also includes the manufacture of a medicine and a method of treatment using such a medicine in the form of a pharmaceutical composition.

Pharmaceutical Combinations and Their Use in Treatment

A pyrrolidine compound of the invention may be combined with a second medicament to form a pharmaceutical combination of the invention. The second medicament is a known agent for treating, controlling, or preventing a malcondition that can be regulated or normalized via inhibition of DPP-IV. The malconditions treated by such combinations are those that can be regulated or normalized via inhibition of DPP-IV and thus are the same as those described above in connection with sole treatment for a pyrrolidine compound of the invention.

The second medicament may include a therapeutically effective amount of a dipeptidyl peptidase-IV inhibitor other than the pyrrolidine compound of the invention. The second medicament preferably may be a known anti-diabetic agent including but not limited to an agent that increases insulin secretion, an agent that increases insulin sensitivity, an agent that reduces the uptake of sugar from the gastrointestinal track, an agent that enhances the effect of endogenous peptides or proteins that play a role in glycemic control, or an agent that acts a replacement therapy for endogenous peptides or proteins that have a known role in glycemic control. Such agents include but are not limited to glyburide (e.g. Micronase and Diabeta), glipizide (e.g. Glucotrol), nateglinide (e.g. Starlix), repaglinide (e.g. Prandin), metformin (e.g. Glucophage), rosiglitazone (e.g. Avandia), acarbose (e.g. Precose), miglitol (e.g. Glyset), exenatide (e.g. Byetta), and insulin (e.g. Humulin and Novolin). Additional exemplary agents include but are not limited to biguanides, chlorpropamide, a glucagon-like peptide-1 (GLP-1) or mimetic thereof such as LY315902 or LY307161, glimepiride, meglitinide, phenformin, pioglitazone, sulfonyl ureas, troglitazone, G1-262570, isaglitazone, JTT-501, NN-2344, L895645, YM-440, R-119702, AJ9677, KAD1129, APR-HO39242, GW-409544, KRP297, AC2993, Exendin-4, and NN2211. The chemical structures, trivial names and pharmacological studies of the foregoing compounds designated by letters and numbers are readily available from the web, for example, by entering the letter/number designation as a search term in the GOOGLE search web site.

A pyrrolidine compound of the invention may be used in combination with one or more second medicaments useful as antidiabetic agents (employed to treat diabetes and related diseases). The second medicament may be administered orally in the same dosage with the pyrrolidine compound of the invention, or in a separate oral dosage form. The pyrrolidine compound of the invention and the second medicament may also be administered, for example by injection, separately, simultaneously or as a mixture.

The pharmaceutical combination of the invention can be formulated as a pharmaceutical composition of a pharmaceutically acceptable carrier along with a pyrrolidine compound of the invention and one or more second medicaments.

In the pharmaceutical combination of the invention, the pyrrolidine compounds of the invention are typically present in a weight ratio to the second medicament of from about 0.01:1 to about 100:1, or preferentially from about 0.1:1 to about 5:1.

The use of a pyrrolidine compound of the invention in combination with one or more other antidiabetic agents may produce antihyperglycemic results greater than that possible from each of these antidiabetic agents alone. The use of a pyrrolidine compound of the invention in combination with one or more other antidiabetic agents may also produce a synergistic effect in that the antihyperglycemic result may be greater than the combined additive antihyperglycemic effects produced by these antidiabetic agents.

The effective amount of a second medicament formulated as a component of the pharmaceutical combination of the invention will follow the recommendations of the second medicament manufacturer, the judgment of the attending physician and will be guided by the protocols and administrative factors for amounts and dosing as indicated in the PHYSICIAN'S DESK REFERENCE (PDR).

The administered dose of a pyrrolidine compound of the invention within the pharmaceutical combination will be carefully adjusted according to age, weight and condition of the patient, as well as the route of administration, dosage form and regimen and the desired result. The ultimate choice of dosage, route and pharmaceutical formulation will determined by the patient's attending physician, whose wisdom and judgment will guide this process.

The compositions described above may be administered in the dosage forms as described above in single or divided doses of one to four times daily. It may be advisable to start a patient on a low dose combination and work up gradually to a high dose combination.

In a further embodiment of the pharmaceutical combinations of the invention, the second medicament can be known anti-obesity agents including but not limited to a beta 3 adrenergic agonist, a lipase inhibitor, a serotonin (and dopamine) reuptake inhibitor, a thyroid hormone receptor-beta agonist, an anorectic agent, a fatty acid oxidation upregulator, or a mixture of any two or more thereof. Suitable, known anti-obesity agents include orlistat, sibutramine, topiramate, axokine, dexamphetamine, phentermine, phenylpropanolamine, famoxin, mazindol, or a mixture of any two or more thereof. These anti-obesity agents may be employed in the same dosage form with a pyrrolidine compound of the invention or in different dosage forms, and the administrative dosages and regimens applied to the anti-obesity agents will follow the recommendations and guides generally known in the art and/or set out in the PDR.

In another embodiment of the pharmaceutical combinations of the invention, the second medicament may be an agent for treating polycystic ovary syndrome. The agent for polycystic ovary syndrome which may be optionally employed in combination with a pyrrolidine compound of the invention may be 1, 2, or more of gonadotropin releasing hormones (GnRH), leuprolide (Lupron®), Clomid®, Parlodel®, oral contraceptives or insulin sensitizers such as PPAR agonists, or other conventional agents for such use which may be employed in amounts specified in the PDR.

Pharmaceutical Compositions of the Invention

The invention includes a pharmaceutical composition containing a pyrrolidine compound of the invention, with or without another medicament as described above, in association with a pharmaceutical carrier. The pharmaceutical composition can be formulated with one or more carriers such as conventional solid or liquid vehicles or diluents and pharmaceutical additives of a type appropriate to the mode of desired administration. The pyrrolidine compound of the invention in a pharmaceutical composition can be administered to mammalian species, especially humans, an oral, buccal, rectal, pulmonary or similar route, for example, in the form of tablets, capsules, granules or powders. It can be administered by a parenteral route in the form of injectable preparations. It can be administered by a transdermal route either by a release patch for transdermal delivery or by electro-transport using an appropriate delivery device.

Pharmaceutical compositions containing a pyrrolidine compound of the invention of the invention may be prepared by conventional techniques, e.g. as described in Remington: The Science and Practice of Pharmacy, 19th Ed., 1995. The compositions may appear in conventional forms, for example capsules, tablets, aerosols, solutions, suspensions or topical applications.

A typical pharmaceutical composition includes a pyrrolidine compound of the invention formulated with a pharmaceutically acceptable carrier which may be an excipient or a diluent, or may be enclosed within a carrier which can be in the form of a capsule, sachet, tablet, paper or other container. In making the composition, conventional techniques for the preparation of pharmaceutical compositions may be used.

For example, a pyrrolidine compound of the invention will usually be mixed with a carrier, or diluted by a carrier, or enclosed within a carrier which may be in the form of an ampoule, capsule, tablet, sachet, paper, or other container. When the carrier serves as a diluent, it may be solid, semi-solid, or liquid material that acts as a vehicle, excipient, or medium for the active compound. The pyrrolidine compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax.

A formulation can be mixed with auxiliary agents which do not deleteriously react with the pyrrolidine compound. Such additives can include wetting agents, emulsifying and suspending agents, salt for influencing osmotic pressure, buffers and/or coloring substances preserving agents, sweetening agents or flavoring agents. A pharmaceutical composition can also be sterilized if desired.

The route of administration may be any route, which effectively transports the pyrrolidine compound of the invention to the appropriate or desired site of action, such as oral, nasal, pulmonary, buccal, rectal, subdermal, intradermal, transdermal or depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, a pharmaceutical composition may be a powder suitable for reconstitution with an appropriate solution as described above. Examples of these include, but are not limited to, freeze dried, rotary dried or spray dried powders, amorphous powders, granules, precipitates, or particulates. For injection, a pharmaceutical composition may optionally contain stabilizers, pH modifiers, surfactants, bioavailability modifiers and combinations of these. A pyrrolidine compound of the invention may be formulated for parenteral administration by injection such as by bolus injection or continuous infusion. A unit dosage form for injection may be in ampoules or in multi-dose containers.

A pharmaceutical composition of the invention may be designed to provide quick, sustained, or delayed release of the active ingredient after administration to the patient by employing procedures well known in the art. Thus, a pharmaceutical composition may also be formulated for controlled release or for slow release.

A pharmaceutical composition of the invention may include, for example, micelles or liposomes, or some other encapsulated form, or may be administered in an extended release form or an enteric coated form to provide a prolonged storage and/or delivery effect. Therefore, the pharmaceutical composition may be compressed into pellets or cylinders and implanted intramuscularly or subcutaneously as depot injections or as implants such as stents. Such implants may employ known inert materials such as silicones and biodegradable polymers, e.g., polylactide-polyglycolide. Examples of other biodegradable polymers include poly(orthoesters) and poly(anhydrides).

A pyrrolidine compound of the invention may be formulated as a sustained release implant or implantable material suitable for continuous administration over a significant period of time. Typical sustained release implants are formed from polymers of pharmaceutically acceptable, biodegradable polymers such as polymers and copolymers of lactic acid, lactide, glycolic acid, glycolide, caproic acid and caprolactone. The dose and amount of pyrrolidine compound of the invention within the implant will be calculated to deliver the desired single dose blood level of pyrrolidine compound.

For nasal administration, a pharmaceutical composition may contain a pyrrolidine compound of the invention dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with a pyrrolidine compound of the invention dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:

| Core: | |
|---|---|
| Pyrrolidine compound of the invention* | 300 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Adde |
| Coating: | |
| HPMC approx. | 9 mg |
| **Mywacett 9-40 T approx. | 0.9 mg |

*Pyrrolidine compound is formulated as free compound or salt thereof.
**Acylated monoglyceride used as plasticizer for film coating.

A typical capsule for oral administration contains a pyrrolidine compound of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of pyrrolidine compound of the invention into a vial, aseptically freeze-drying and sealing. For use, the contents of the vial are mixed with 2 mL of physiological saline, to produce an injectable preparation.

A pyrrolidine compound of the invention may be administered to a mammal, especially a human in need of such treatment, prevention, elimination, alleviation or amelioration of the various malconditions mentioned above. Such mammals include also animals, both domestic animals, e.g. household pets, farm animals, and non-domestic animals such as wildlife.

A pyrrolidine compound of the invention is effective over a wide dosage range. For example, in the treatment of adult humans, dosages from about 0.5 to about 2000 mg, preferably from about 10 mg to about 1000 mg, per day, more preferably about 50 to 750 mg per day may be used. A typical dosage is about 50 mg to about 750 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, a pyrrolidine compound of the invention is dispensed in unit dosage form including from about 0.5 to about 2000 mg of active ingredient together with a pharmaceutically acceptable carrier per unit dosage.

Usually, a dosage form suitable for oral, nasal, pulmonary or transdermal administration includes from about 0.5 mg to about 2000 mg, preferably from about 10 mg to about 1000 mg per day, more preferably from about 50 mg to about 750 mg of a pyrrolidine compound admixed with a pharmaceutically acceptable carrier or diluent.

A pharmaceutical combination of the invention may be formulated as a pharmaceutical composition employing all of the embodiments, carriers, route designs and the like described above for formulation of a pharmaceutical composition of a pyrrolidine compound alone.

The invention also encompasses prodrugs of a pyrrolidine compound of the invention which on administration undergo chemical conversion by metabolic processes before becoming active pharmacological substances. In general, such prodrugs will be functional derivatives of a pyrrolidine compound of the invention which are readily convertible in vivo into a pyrrolidine compound of the invention. Conventional procedures for the selection and preparation of suitable prodrug derivatives are described, for example, in "Design of Prodrugs", ed. H. Bundgaard, Elsevier, 1985.

The invention also encompasses active metabolites of a pyrrolidine compound of the invention.

Thus, another aspect of the invention provides a pharmaceutical composition of a pyrrolidine compound of the invention, alone or in combination with another type antidiabetic agent and/or other type therapeutic agent.

Additional embodiments of the invention are represented by:

A pharmaceutical composition including a pyrrolidine compound of the invention, as described above, together with at least one pharmaceutically acceptable carrier or diluent;

Methods of making a pharmaceutical composition of a pyrrolidine compound of the invention wherein the pharmaceutically acceptable carrier or diluent is suitable for oral administration;

Methods of making a pharmaceutical composition of a pyrrolidine compound of the invention suitable for oral administration further including the step of formulating the composition into a tablet or capsule;

Methods of making a pharmaceutical composition of a pyrrolidine compound of the invention wherein the pharmaceutically acceptable carrier or diluent is suitable for parenteral administration;

Methods of making a pharmaceutical composition of a pyrrolidine compound of the invention suitable for parenteral administration further including the step of lyophilizing the composition to form a lyophilized preparation.

DPP-IV inhibitory activity of the pyrrolidine compound of the invention may be determined by use of an in vitro assay system. Inhibition constants (Ki or $IC_{50}$ values) for the DPP-IV inhibitors of the invention may be determined by the method described below.

A further detailed description of the invention is given with reference to the following non-limiting examples.

EXAMPLES

Example 1

Synthesis of Pyrrolidine Compounds of the Invention (2R)-boroPro-(1S,2S,3R,5S)-pinanediol ester, hydrochloride (2): A flame dried round bottom flask equipped with a magnetic stir bar was charged with N-Boc-pyrrolidine (20 g, 117 mmol, 1 eq) and dry THF (60 mL) under a nitrogen atmosphere. The clear colorless solution was cooled to −78° C. and a solution of s-BuLi (100 mL of a 1.4 M solution in cyclohexane, 140 mmol) was added slowly over a 30 minute period. The light orange colored solution was stirred at −78° C. for 3 hours followed by treatment with B(OMe)$_3$ (39 mL, 350 mmol) after which the cooling bath was removed and the clear colorless solution slowly warmed to 0° C. Upon reaching 0° C., the reaction was quenched with a small amount of water (~2 mL), allowed to warm to room temp then extracted into 2 N NaOH (250 mL) and backwashed with additional EtOAc (150 mL). The aqueous phase was acidified to pH 3 by the addition of 2 N HCl and then extracted with EtOAc (3×120 mL). The organic extracts were combined and dried over Na$_2$SO$_4$ and concentrated to produce the free boronic acid (22.08 g, 103 mmol) as a sticky white solid in 88% yield. Without further purification the boronic acid was dissolved in tert-butyl methyl ether (150 mL) and with constant stirring (+)-pinanediol (17.5 g, 103 mmol) was added at room temperature. After 18 hr the ether was removed and the (+)-pinanediol boronic ester was purified by column chromatography (silica gel, 1:3 hexanes/EtOAc) to give a clear thick oil (26.84 g, 76.8 mmol, 76% yield, R$_f$=0.6 using a 2:1 hexane/ethyl acetate eluant, made visual via I$_2$ and/or PMA stain). Removal of the Boc protecting group was achieved by dissolving the oil in dry ether, cooling to 0° C. in an ice bath and with constant stirring dry HCl (g) was bubbled into the solution for 10 minutes. After 2 hours a white precipitate developed in the flask and the ether and excess HCl were removed in vacuo to afford the racemic HCl salt as a white solid. Crystallization and isolation of the desired isomer was performed by dissolving the HCl salt in a minimal amount of dichloromethane (250 mL) with gentle heating to facilitate a homogenous solution followed by continuous stirring for 8 hours to yield a fluffy white precipitate that was collected by vacuum filtration, dried and then dissolved in minimal 2-propanol (~200 mL) with gentle heating until homogenous. The alcoholic solution was stirred over night and the resulting white precipitate was collected by vacuum filtration affording isomerically pure 2 as a white solid. (7.0 g, 27 mmol, 23% yield). $^1$H NMR (400 MHz, D$_2$O) δ 4.28 (d, J=8.0 Hz, 1H), 3.06 (m, 3H), 2.18 (m, 1H), 1.96 (m, 2H), 1.78 (m, 3H), 1.62 (m, 2H), 1.21 (s, 3H), 1.05 (m, 5H), 0.84 (d, J=12 Hz, 2H), 0.71 (s, 2H), 0.62 (s, 3H).

(2R)-1-(2-Chloroacetyl)-boroPro-(1S,2S,3R,5S)-pinanediol ester (3): To a solution of 2 (36.7 g, 129.3 mmol) dissolved in dry CH$_2$Cl$_2$ (200 mL) cooled to 0° C. was added chloroacetyl chloride (12.34 mL, 155.2 mmol) under a blanket of N$_2$. To this was slowly dripped 4-methylmorpholine (42.4 mL, 182 mmol) to give an almost clear light orange solution that was warmed to room temp. After 30 minutes the solution was cooled again to 0° C. and 200 mL of a 0.2 N solution of HCl was added and the organic layers separated, dried and concentrated to give a dark red oil that was a single spot by TLC (2:1 hex/EtOAc, R$_f$=0.22, made visual via I$_2$ and/or PMA stain) and was used in the next step without further purification. $^1$H NMR (400 MHz, CDCl$_3$) δ0.80 (s, 3H), 1.25 (m, 1H), 1.26 (s, 3H), 1.42 (s, 3H), 1.75-1.96 (m, 4H), 1.98-2.10 (m, 3H), 2.12-2.20 (m, 1H), 2.29-2.35 (m, 1H), 3.12-3.16 (m, 1H), 3.47-3.53 (m, 1H), 3.58-3.63 (m, 1H), 3.97-4.05 (q, 2H), 4.30-4.32 (d, 1 H).

(2R)-1-{2-[(3R)-1-tert-Butoxycarbonyl-pyrrolidine-3-ylamino]-acetyl}-pyrrolidine-2-boronic acid (1S,2S,3R,5S)-pinanediol ester (6): Compound 3 (22.7 g, 70 mmol) was dissolved in dry THF (600 mL) followed by addition of excess K$_2$CO$_3$ and cooled to 0° C. before addition of (3R)-3-amino-pyrrolidine-1-carboxylic acid tert-butyl ester (14.35 g, 77.2 mmol). The reaction mixture was warmed to room temperature and stirred for an additional 2.5 days. When TLC indicated all starting material was consumed (10% MeOH in CH$_2$Cl$_2$, product was visualized with I$_2$ stain and appeared as two separate spots (open and closed) R$_f$=0.55). The mixture was filtered through a celite pad, washed with 5% MeOH in CH$_2$Cl$_2$ (500 mL) and concentrated to yield a sticky, lightly yellow solid. The solid was dissolved in minimal CH$_2$Cl$_2$ followed by column chromatography (silica gel 60, eluted with 5% MeOH in CH$_2$Cl$_2$) solution to give 12.1 g of 6. MS m/z (rel intensity) 476 (M+1)$^+$ (100), 376 (74), 239 (38), 224 (67), 155 (55).

(2R)-1-{2-[(3R)-Pyrrolidin-3-ylamino]-acetyl}-pyrrolidine-2-boronic acid (7): A solution of compound 6 in 4N HCl in dioxane was stirred at room temperature for 4 h. The solvent was removed under vacuum and the resulting yellow residue was dissolved in 1N HCl and an equal amount of hexane. To this bi-phasic solution was added phenyl boronic acid and the mixture was stirred vigorously. The hexane layer was periodically removed and replaced with fresh hexane 6 times over a 24-hour period and progress monitored via LCMS. The aqueous layer was separated and applied to a Dowex 50-X2-100 ion exchange column (H+ form) and eluted with water until the eluant was neutral. Then the eluant was changed to aqueous ammonium hydroxide (2% vbw) followed by lyophilization of the appropriate fractions to yield 7 as a white crystalline solid (Table 1). TFA salt $^1$H-NMR (500 MHz, CD$_3$OD) δ 4.13 (m, 1H), 4.08 (bs, 2H), 3.76 (dd, J=13.0, 8.0 Hz, 1H), 3.55 (m, 3H), 3.41 (m, 2H), 3.27 (m, 1H), 2.53 (m, 1H), 2.26 (m, 1H), 2.10 (m, 2H), 1.99 (m, 1H), 1.75 (m, 1H). MS m/z (rel intensity) 224 (M−17) (100), 206 (25), 180 (29), 155 (70).

(2R)-1-{2-[(3)-1-tert-Butoxycarbonyl-pyrrolidin-3-ylamino]-acetyl}-pyrrolidine-2-boronic acid (1S,2S,3R,5S)-pinanediol ester (8): The protocol described above for the synthesis of 6 was followed employing (3S)-3-amino-pyrrolidine-1-carboxylic acid tert-butyl ester in place of (3R)-3-amino-pyrrolidine-1-carboxylic acid tert-butyl ester. Compound 8 was obtained as an oil. MS m/z (rel intensity) 476 (M+1)$^+$ (100), 376 (74), 239 (38), 224 (67), 155 (55).

(2R)-1-{2-[(3S)-Pyrrolidin-3-ylamino]-acetyl}-pyrrolidine-2-boronic acid (9): The protocol described above for the synthesis of 7 was followed to produce 9 (table 1). 8.TFA salt $^1$H-NMR (500 MHz, CD$_3$OD) δ 4.12 (m, 3H), 3.76 (m, 1H), 3.54 (m, 3H), 3.41 (m, 2H), 3.26 (m, 1H), 2.55 (m, 1H), 2.28 (m, 1H), 2.05 (m, 3H), 1.74 (m, 1H). MS m/z (rel intensity) 241 (M) (27), 224 (100), 209 (73), 155 (47).

TABLE 1

| Compound No. | Name | Structure | LC-MS |
|---|---|---|---|
| 7 | (2R)-1-{2-[(3R)-Pyrrolidin-3-ylamino]-acetyl}-pyrrolidine-2-boronic acid | 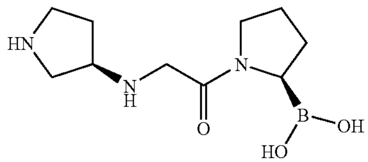 | 242 (M + 1) (100), 224 (9) |
| 9 | (2R)-1-{2-[(3S)-Pyrrolidin-3-ylamino]-acetyl}-pyrrolidine-2-boronic acid | 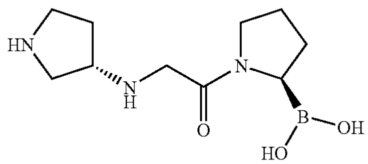 | 242 (M + 1) (100), 224 (19) |

Example 2

DPP-IV Inhibitory Assays

The purification of porcine DPP-IV and the enzyme assay under steady state conditions are described in (1) Rahfeld, J. Schutkowski, M., Faust, J., Neubert., Barth, A., and Heins, J. (1991) Biol. Chem. Hoppe-Seyler, 372, 313-318; and (2) Nagatsu, T., Hino, M., Fuyamada, H., Hayakawa, T., Sakakibara, S., Nakagawa, Y., and Takemoto, T. (1976) Anal. Biochem., 74, 466-476, respectively. Human DPP-IV is also commercially available from, e.g., Research Diagnostics.

The activity of human DPP-IV was measured in vitro by its ability to cleave the synthetic substrate Gly-Pro-AMC. Cleavage of Gly-Pro-AMC by DPP-IV liberates the product AMC (7-amino-4-methyl coumarin), whose rate of appearance is directly proportional to the enzyme activity. Inhibition of the enzyme activity by specific enzyme inhibitors slows down the generation of AMC. Stronger interaction between an inhibitor and the enzyme results in a slower rate of generation of AMC. Thus, the degree of inhibition of the rate of accumulation of AMC is a direct measure of the strength of enzyme inhibition. The accumulation of AMC is measured fluorometrically. The $IC_{50}$ (concentration of test compound at which 50% of the enzyme activity is inhibited) for each compound is determined by incubating fixed amounts of enzyme with several different concentrations of inhibitor. The inhibition constant, Ki, can be determined for each compound by incubating fixed amounts of enzyme with several different concentrations of inhibitor and substrate.

The compounds of the invention were tested for their ability to inhibit the activity of purified DPP-IV using the following methods. DPP-IV enzyme activity was determined by a fluorometric assay with the substrate Gly-Pro-AMC which is cleaved by DPP-IV to release the fluorescent AMC leaving group. Free AMC (7-amino-4-methyl coumarin) was measured using an excitation wavelength of 380 nm and an emission wavelength of 460 nm with a Victor-II fluorescent reader. Stock solutions of DPP-IV (1 ng/μl, pH 8.0) and Gly-Pro-AMC substrate (400 μM) in 25 mM Tris buffer (pH 8.0) were prepared separately. Test compounds were dissolved in DMSO or in 50 mM glycine buffer (pH 3.0). The assay was performed by diluting the DPP-IV stock (10 μl) into 25 mM Tris buffer (77.5 μl) followed by addition of test compound (2.5 μl) at 26° C. After 10-minutes substrate was added (10 μl) and allowed to react for 20-minutes at 26° C. before free AMC was measured. $IC_{50}$ values were determined in triplicate, using a minimum of six different inhibitor concentrations. $IC_{50}$ values were calculated using Nonlinear Regression Analysis (GraphPad, Prism, San Diego, Calif.).

Compounds 7 and 9 were tested in vitro as inhibitors of DPP-IV as described herein and each displayed an $IC_{50}$ of 1 μM or less.

Example 3

DPP-VII, DPP-VIII, DPP-IX, and FAP Inhibitory Assays

Recombinant DPP-VII, DPP-VIII, DPP-IX, and FAP enzymes were prepared as follows. The full length cDNAs for human DPP-VII, DPP-VIII, DPP-IX, and FAP were obtained from Open Biosystems. The cDNAs were cloned into the pFastBac vector with the addition of an N-terminal FLAG tag on DPP-VII, C-terminal 6×His tags on DPP-VIII and DPP-IX, and an N-terminal 6×His tag on FAP (Sun 2002, Qi 2003, and Chen 2004). Baculovirus was prepared using the Bac-to-Bac Baculovirus Expression System (Invitrogen). The cDNAs in the final baculovirus constructs were sequence verified.

To express the recombinant DPPs from the baculovirus constructs, S9 insect cells (cells and Sf-900 SFM media purchased from Invitrogen) were grown to mid log phase at 27° C. with shaking at 125 rpm and then adjusted to 2×10E6/ml just prior to baculovirus infection. Infection with DPP-VII, DPP-VIII, DPP-IX, and FAP baculoviral constructs were all performed at an MOI of 4. The infected cells were grown for 48 hours and the cell pellets harvested and frozen until purification. DPP-VII was purified using anti-FLAG immunoaffinity gel according to the manufacturer's instructions. DPP-VIII, DPP-IX, and FAP were purified using a B-PER 6×His Fusion Protein Column Purification Kit from Pierce.

The activity of DPP-VII, DPP-VLII, DPP-IX and FAP was measured in vitro by its ability to cleave the synthetic substrates Lys-Pro AMC (DPP-VH) and Ala-Pro AMC (DPP-VJII, DPP-DC and FAP) (substrates purchased from Enzyme Systems). Recombinant DPPs were diluted in reaction buffer to give fluorescence values of 5000-20000 counts in the "enzyme only wells" 20 min after addition of substrate at 27° C. Reaction buffers were 25 mM (2-(4-Morpholino)-

Ethane Sulfonic Acid), pH 5.5 for DPP-VII, 25 mM Tris, pH 8, 1% Triton X-100, 100 mM NaCl for DPP-VIII, and 25 mM Tris pH 8 for DPP-IX and FAP. Test wells in a 96-well microtiter plate contained 88 μL of diluted DPP and 2.5 μL of titrated compound in 50 mM glycine, pH 2.6. "Enzyme only" wells contained 88 μL of diluted DPP and 2.5 μL of glycine buffer. "No enzyme" wells contained 88 μL of reaction buffer without DPP and 2.5 μL of glycine buffer. All assays were done in triplicate. The plate was incubated at 27° C. for 10 min and then cooled on ice for 10 min. Ten microliters of substrate diluted in reaction buffer (40 μM final concentration) without Triton or NaCl were ten added to all wells followed by incubation at 27° C. for 20 min. Fluorescence in each well was measured at settings of 380/460 nm. $IC_{50}$ calculations were performed by non-liner regression analysis using Prism software (GraphPad).

Example 4

DPP Selectivity of Boronic Acids

Using the methods described above, the DPP-IV, VII, VIII, IX and FAP inhibitory activities of compounds 7 and 9 were compared to the closely related analogues shown in Table 2.

TABLE 2

Other Boronic Acid Inhibitors

| Compound Number | Structure |
|---|---|
| 5 | 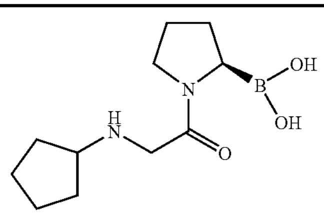 |
| 14 | 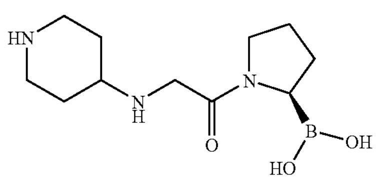 |
| 15 | 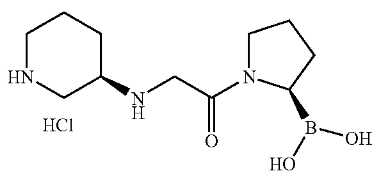 |
| 16 | 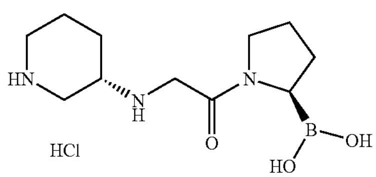 |
| 17 | |
| 18 | |
| 19 | |
| 20 | |

The selectivity ratio value was obtained by dividing the $IC_{50}$ value for DPP-VII, DPP-VIII, DPP-IX or FAP by the $IC_{50}$ value for DPP-IV and assigned a selectivity ratio defined as A≦1; 1<B≦10; 10<C≦50; D>50. Results are summarized in Table 3.

TABLE 3

DPP Selectivity Ratios

| Compound No. | Selectivity Ratios* | | | |
|---|---|---|---|---|
| | DPP-VII | DPP-VIII | DPP-IX | FAP |
| 5 | A | B | A | B |
| 7 | C | D | C | D |
| 9 | C | C | A | C |
| 14 | A | B | A | D |
| 15 | A | B | A | C |
| 16 | B | C | A | C |
| 17 | B | B | A | C |
| 18 | B | C | A | C |

TABLE 3-continued

| Compound | DPP Selectivity Ratios | | | |
|---|---|---|---|---|
| | Selectivity Ratios* | | | |
| No. | DPP-VII | DPP-VIII | DPP-IX | FAP |
| 19 | A | B | B | B |
| 20 | A | A | A | B |

*Selectivity ratios: A ≦ 1; 1 <B ≦ 10; 10 < C ≦ 50; D > 50

Compounds 7 and 9, incorporating pyrrolidine, show greatly improved selectivity in contrast to their closely related analogues. For example, compounds 7 and 9 show excellent selectivity for DPP-IV relative to DPP-VIII. Replacement of the 3-aminopyrrolidine with cyclopentyl 5,4-piperidinyl 14, 3R-piperidinyl 15, or 3S-piperidinyl 16 (Table 2) maintains inhibition of DPP-IV. However, compounds 5, 14, 15, and 16 are significantly less selective towards the other dipeptidyl peptidases with one or more exhibiting selectivity ratios ≦1; and two or more exhibiting selectivity ratios ≦10. Thus, examples of the claimed compounds (compound 7 and 9) demonstrate unexpected selectivity towards the other dipeptidyl peptidases while maintaining potency against DPP-IV, while the close structural analogues of the selective compounds of the invention exhibit significant activity against one or more of the other dipeptidyl peptidases.

Also, addition of further moieties at positions on the pyrrolidine ring produces compounds with reduced selectivity towards the other dipeptidyl peptidases. Alkylation of the pyrrolidine nitrogen yielding compounds 17 and 18, acylation of the pyrrolidine nitrogen yielding compound 19 or incorporation of a carboxamide yielding compound 20 all lead to a substantial loss of selectivity. See Table 2 for the structures of these compounds.

Example 5

In Vivo Toxicity of Boronic Acids

To determine toxicity of boronic acids in rats, the Zucker Diabetic Fatty (ZDF) rat model was used. After overnight fasting, adult rats were orally administered either vehicle or test compound at the indicated doses once a day and twice a day. Animals were monitored for clinical signs at 1, 2, 4 and 8 hour time intervals following the treatment regimen and blood samples were collected. Oral doses of compound 5 at 10 mg/kg and PT100 (valboropro, Bachovchin et al., PNAS, 88:1556, 1991; Bachovchin et al. J. Med. Chem, 39:2087, 1996) at 1 mg/kg caused acute toxicity (death) 4-24 hrs post-dose in all Zucker Obese Fatty rats tested. By contrast, inventive compound 7 was well tolerated at doses up to 80 mg/kg (≧20% DPP-IV inhibition for 24 hrs at all doses).

To assess toxicity of boronic acids in dogs, IV dosing studies were performed. Compound 7, of the invention, was compared with the closely related analog, compound 5. Compound 5 is a potent inhibitor of DPP-IV and all the other DPPs, whereas compound 7 is a potent and selective inhibitor of DPP-IV. When compound 5 was administered to dogs at 0.2 mg/kg or higher, increasing toxicity was observed with severe emesis and diarrhea observed at 2 mg/kg while a dose of 0.1 mg/kg did not elicit any toxicities. A comparison of the plasma concentrations of 5 at 0.1 and 0.2 mg/kg demonstrated that the time above the DPP-VIII $IC_{90}$ was 2 and 4 hours respectively and greater than 14 hours for DPP-IX, the DPP with the lowest selectivity ratio (Table 3). This observation coupled with the 2-4 hour onset of toxicity demonstrates that activity against DPP-VIII mediates the observed toxicity. Compound 7, a selective DPP-IV inhibitor, when administered at a dose of (6.0 mg/kg), a dose that resulted in plasma levels at the $IC_{90}$ for DPP-VIII for less than 2 hours, showed no toxicity confirming the improved safety of compounds of the invention over non-selective DPP inhibitors.

While the invention has been described and exemplified in sufficient detail for those skilled in this art to make and use it, various alternatives, modifications, and improvements will be apparent to those skilled in the art without departing from the spirit and scope of the claims.

All patents and publications are herein incorporated by reference to the same extent as if each individual publication was specifically and individually indicated to be incorporated by reference.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A pyrrolidine compound represented by formula I:

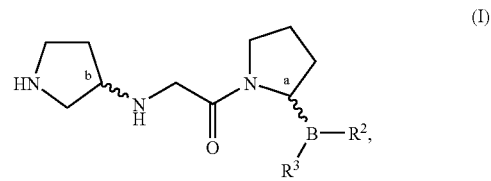

a cyclic isomer thereof, any pharmaceutically acceptable salt thereof, any prodrug thereof, or any solvate thereof; wherein $R^2$ and $R^3$ independently or together are —OH,—O⁻M⁺ wherein M⁺ is a cation, a hydroxyl bearing a boronic acid protecting group, or a group capable of being hydrolyzed to a hydroxyl group in an aqueous solution at physiological pH or in biological fluids; and the wavy lines at asymmetric carbons $C^a$ and $C^b$ independently indicate for each asymmetric carbon an R configuration, an S configuration, or a mixture of both configurations such that all stereoisomers and all stereomeric mixtures are included.

2. A pyrrolidine compound of claim 1 having an R configuration at $C^a$.

3. The pyrrolidine compound of claim 2 having an R configuration at $C^b$.

4. The pyrrolidine compound of claim 2 having an S configuration at $C^b$.

5. An optically enriched stereoisomer of the pyrrolidine compound of claim 1.

6. A stereomeric mixture of two or more stereoisomers of the pyrrolidine compound of claim 1, wherein at least one of the asymmetric carbons, $C^a$ or $C^b$ has both R and S configurations.

7. A stereomeric mixture of claim 6, which is a mixture of two diastereoisomers, an enantiomeric pair, a racemic mixture, a mixture of an enantiomeric pair plus a diastereomer, or an optically active mixture of at least two stereoisomers.

8. A stereomeric mixture of claim 6, wherein one stereoisomer predominates and the predominant isomer has an R configuration at $C^a$ and an R or S configuration at $C^b$.

9. A stereomeric mixture of claim 8, wherein the predominant isomer has an R configuration at $C^b$.

10. A stereomeric mixture of claim 6, wherein two optical isomers predominate, one having R configurations at $C^a$ and $C^b$, and one having an R configuration at $C^a$ and an S configuration at $C^b$.

11. A pyrrolidine compound of claim 1 having the structure:

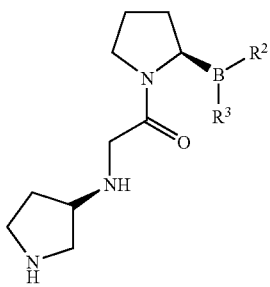

and having a stereomeric purity of at least about 55%.

12. A pyrrolidine compound of claim 11 having a stereomeric purity of at least about 90%.

13. A pyrrolidine compound of claim 11 having a stereomeric purity of at least about 98%.

14. A pyrrolidine compound of claim 1 having the structure:

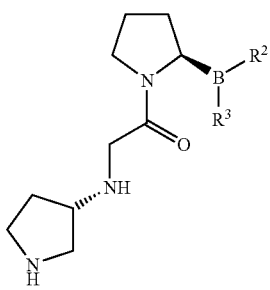

and having a stereomeric purity of at least about 55%.

15. A pyrrolidine compound of claim 1 wherein the cyclic isomer form is represented by formula V:

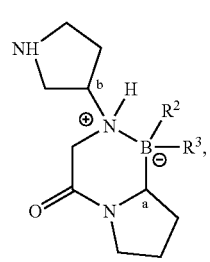

(V)

wherein the asymmetric carbons $C^a$ and $C^b$ independently have an R configuration, an S configuration, or a mixture of both configurations such that all stereoisomers and all stereomeric mixtures are included.

16. A pharmaceutical combination comprising:
   (a) a pyrrolidine compound represented by formula I:

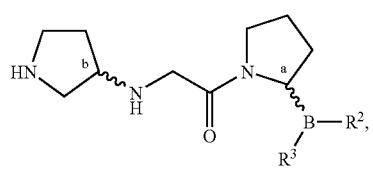

(I)

a cyclic isomer thereof, any pharmaceutically acceptable salt thereon any prodrug thereof, or any solvate thereof; wherein $R^2$ and $R^3$ independently or together are —OH, —O⁻M⁺ wherein M⁺ is a cation, a hydroxyl bearing a boronic acid protecting group, or a group capable of being hydrolyzed to a hydroxyl group in an aqueous solution at physiological pH or in biological fluids, and the wavy lines at asymmetric carbons $C^a$ and $C^b$ independently indicate for each asymmetric carbon an R configuration, an S configuration, or a mixture of both configurations such that all stereoisomers and all stereomeric mixtures are included; and
   (b) a known second medicament that increases insulin secretion, increases insulin sensitivity, reduces the uptake of sugar from the gastrointestinal track, enhances the effect of endogenous peptides or proteins that affect glycemic control, provides a replacement for endogenous peptides or proteins that affect glycemic control, or any combination thereof.

17. A pharmaceutical combination of claim 16 wherein the second medicament is the antidiabetic agent.

18. A pharmaceutical combination of claim 17, wherein the weight ratio of the compound of formula I and the antidiabetic agent is from about 0.01:1 to about 100:1.

19. A pharmaceutical combination of claim 16, wherein the second medicament is glyburide, glipizide, nateglinide, repaglinide, metformin, pioglitazone, rosiglitazone, acarbose, miglitol, exenatide, insulin, or any combination thereof.

20. A pharmaceutical combination of claim 16 wherein the second medicament is suitable for treatment of a diabetes-associated condition.

21. A pharmaceutical composition comprising:
(a) a pyrrolidine compound represented by formula I:

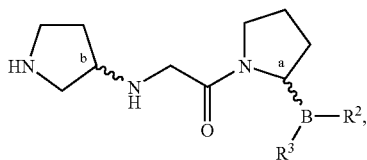
(I)

or a cyclic isomer thereof, or any pharmaceutically acceptable salt thereof, any prodrug thereof, or any solvate thereof; wherein $R^2$ and $R^3$ independently or together are —OH, —$O^-M^+$ wherein $M^+$ is a cation, a hydroxyl bearing a boronic acid protecting group, or a group capable of being hydrolyzed to a hydroxyl group in an aqueous solution at physiological pH or in biological fluids, and the wavy lines at asymmetric carbons $C^a$ and $C^b$ independently indicate for each asymmetric carbon an R configuration, an S configuration, or a mixture of both configurations such that all stereoisomers and stereomeric mixtures are included; and
(b) a pharmaceutically acceptable carrier.

22. A pharmaceutical composition of claim 21, further comprising (c) a second medicament selected from the group consisting of a known second medicament that increases insulin secretion, increases insulin sensitivity, reduces the uptake of sugar from the gastrointestinal track, enhances the effect of endogenous peptides or proteins that affect glycemic control, or provides a replacement for endogenous peptides, proteins that affect glycemic control, or any combination thereof.

23. A process for manufacture of a pharmaceutical composition of claim 21 comprising combining a pyrrolidine compound with a pharmaceutically acceptable carrier or diluent.

24. A process of claim 23, wherein the pharmaceutically acceptable carrier or diluent is suitable for oral administration or parenteral administration.

25. A process of claim 23, further comprising the step of formulating the composition into a tablet or capsule.

26. A process of claim 23, further comprising the step of lyophilizing the composition or the compound of formula I.

27. A pyrrolidine compound of claim 1, wherein $R^2$ and $R^3$ independently or together are the boronic acid protecting group formed from (+)-pinanediol; pinacol; 1,2-dicyclohexyl-ethanediol; 1,2-ethanediol; 2,2-diethanolamine; 1,3-propanediol; 2,3-butanediol; diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol.

* * * * *

UNITED STATES PATENT AND TRADEMARK OFFICE
CERTIFICATE OF CORRECTION

PATENT NO. : 7,317,109 B2
APPLICATION NO. : 11/381085
DATED : January 8, 2008
INVENTOR(S) : Campbell et al.

It is certified that error appears in the above-identified patent and that said Letters Patent is hereby corrected as shown below:

On title page on page 2, item 56 under "Other Publications", in column 2, line 36, delete "$Na^=$/blle" and insert -- $Na^+$/blle --, therefor.

On page 2, item 56 under "Other Publications", in column 2, line 46, delete "Immunosuppresive" and insert -- Immunosuppressive --, therefor.

On page 2, item 56 under "Other Publications", in column 2, line 63, delete "activated" and insert -- Activated --, therefor.

Column 1, line 48, delete "glucagon like" and insert -- glucagon-like --, therefor.

Column 4, line 49, after "2-chloroacetyl," delete "chloracetyl,".

Column 4, line 50, delete "trichloracetyl," and insert -- trichloroacetyl, --, therefor.

Column 4, lines 62-63, delete "$\alpha\alpha$–dimethyl–3,5–dimethoxvbenzyloxvcarbonyl," and insert -- $\alpha,\alpha$–dimethyl–3,5–dimethoxybenzyloxycarbonyl, --, therefor.

Column 4, line 66, delete "trichioroethoxycarbonyl," and insert -- trichloroethoxycarbonyl, --, therefor.

Column 6, line 29, delete "(1999)," and insert -- (1999)), --, therefor.

Column 9, line 23, delete "60/704,3 80," and insert -- 60/704,380, --, therefor.

Column 14, line 62, delete "poly(orthoesters)" and insert -- poly (orthoesters) --, therefor.

Column 14, line 62, delete "poly(anhydrides)." and insert -- poly (anhydrides). --, therefor.

Column 16, line 66, delete "DPP-1V" and insert -- DPP-IV --, therefor.

Column 18, line 13, delete "1 H)." and insert -- 1H). --, therefor.

Column 18, line 14, delete "pyrrolidine" and insert -- pyrrolidin --, therefor.

Column 18, line 48, delete "$^1$H-NMR" and insert -- $^1$H NMR --, therefor.

Column 18, line 53, delete "(3)" and insert -- (3S) --, therefor.

UNITED STATES PATENT AND TRADEMARK OFFICE
CERTIFICATE OF CORRECTION

PATENT NO. : 7,317,109 B2
APPLICATION NO. : 11/381085
DATED : January 8, 2008
INVENTOR(S) : Campbell et al.

It is certified that error appears in the above-identified patent and that said Letters Patent is hereby corrected as shown below:

Column 18, line 64, delete "$^1$H-NMR" and insert -- $^1$H NMR --, therefor.

Column 20, line 60, delete "DPP-VLII," and insert -- DPP-VIII, --, therefor.

Column 20, line 62, delete "(DPP-VH)" and insert -- (DPP-VII) --, therefor.

Column 20, line 63, delete "(DPP-VJII, DPP-DC" and insert -- (DPP-VIII, DPP-IX --, therefor.

Column 21, line 13, delete "ten" and insert -- then --, therefor.

Column 21, line 16, delete "non-liner" and insert -- non-linear --, therefor.

Column 23, line 11, delete "1 <B" and insert -- 1 < B --, therefor.

Column 23, line 17, delete "5,4" and insert -- 5, 4 --, therefor.

Column 23, line 55, delete "(≥20%" and insert -- (≥90% --, therefor.

Column 24, line 50, in Claim 1, delete "—OH,—O$^-$M$^+$" and insert -- —OH, —O$^-$M$^+$ --, therefor.

Column 25, line 3, in Claim 6, delete "C$^b$" and insert -- C$^b$, --, therefor.

Column 26, line 35, in Claim 16, delete "thereon" and insert -- thereof, --, therefor.

Signed and Sealed this

Sixth Day of May, 2008

JON W. DUDAS
*Director of the United States Patent and Trademark Office*